United States Patent
Ishii

(10) Patent No.: US 8,632,247 B2
(45) Date of Patent: Jan. 21, 2014

(54) RADIATION IMAGING SYSTEM AND METHOD FOR DETECTING POSITIONAL DEVIATION

(75) Inventor: Hiroyasu Ishii, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 419 days.

(21) Appl. No.: 13/016,979

(22) Filed: Jan. 29, 2011

(65) Prior Publication Data

US 2011/0235779 A1 Sep. 29, 2011

(30) Foreign Application Priority Data

Mar. 26, 2010 (JP) .................. 2010-072070
Sep. 30, 2010 (JP) .................. 2010-220653

(51) Int. Cl.
*A61B 6/00* (2006.01)

(52) U.S. Cl.
USPC ........................................... 378/207; 378/62

(58) Field of Classification Search
USPC ................... 378/36, 37, 62, 82, 207
See application file for complete search history.

(56) References Cited

U.S. PATENT DOCUMENTS

| | | | |
|---|---|---|---|
| 7,180,979 B2 | 2/2007 | Momose | |
| 2011/0243300 A1* | 10/2011 | Kaneko et al. | 378/36 |
| 2012/0148021 A1* | 6/2012 | Ishii | 378/62 |
| 2012/0163537 A1* | 6/2012 | Iwakiri et al. | 378/62 |
| 2013/0077747 A1* | 3/2013 | Kamono et al. | 378/62 |

FOREIGN PATENT DOCUMENTS

| | | |
|---|---|---|
| JP | 2008-200360 A | 9/2008 |
| WO | WO 2004/058070 A1 | 7/2004 |

OTHER PUBLICATIONS

C. David, et al. "Differential x-ray phase contrast imaging using a shearing interferometer" Applied Physics Letters, vol. 81, No. 17, Oct. 2002, pp. 3287-3289.

Hector Canabal, et al., "Improved phase-shifting method for automatic processing of moiré deflectograms" Applied Optics, vol. 37, No. 26, Sep. 1998, pp. 6227-6233.

\* cited by examiner

*Primary Examiner* — Glen Kao
(74) *Attorney, Agent, or Firm* — McGinn IP Law Group, PLLC

(57) ABSTRACT

A radiation imaging system includes an X-ray source, first and second absorption gratings disposed in a path of X-rays emitted from the X-ray source, and an FPD. The second absorption grating is slid stepwise in an X direction relative to the first absorption grating. Whenever the second absorption grating is slid, the FPD captures a fringe image. From the captured plural fringe images, an intensity modulation signal of each pixel is obtained. A positional deviation detector calculates an amplitude value of the intensity modulation signal. The positional deviation detector compares a measurement of the amplitude value with predetermined first and second threshold values. If the measurement is less than the first threshold value, a warning signal is outputted. If the measurement is less than the second threshold value, an error signal is outputted.

11 Claims, 9 Drawing Sheets

RADIATION IMAGING SYSTEM AND METHOD FOR DETECTING POSITIONAL DEVIATION

BACKGROUND OF THE INVENTION

1. Field of the Invention

The present invention relates to a radiation imaging system that carries out radiography with the use of radiation such as X-rays. More specifically, the present invention relates to the radiation imaging system for phase imaging that is provided with gratings disposed between a radiation source and a radiation image detector, and a method for detecting positional deviation between the gratings.

2. Description Related to the Prior Art

X-rays are used as a probe for imaging inside of an object without incision, due to the characteristic that attenuation of the X-rays depends on the atomic number of an element constituting the object and the density and thickness of the object. Radiography with the use of the X-rays is widely available in fields of medical diagnosis, nondestructive inspection, and the like.

In a conventional X-ray imaging system for capturing an X-ray image of the object, the object to be examined is disposed between an X-ray source for emitting the X-rays and an X-ray image detector for detecting the X-rays. The X-rays emitted from the X-ray source are attenuated (absorbed) in accordance with the characteristics (atomic number, density, and thickness) of material of the object present in an X-ray path, and are then incident upon pixels of the X-ray image detector. Thus, the X-ray image detector detects the X-rays, and the X-ray image is formed from a detection signal. There are some types of X-ray image detectors in widespread use, such as a combination of an X-ray intensifying screen and a film, an imaging plate containing photostimulated phosphor, and a flat panel detector (FPD) that is composed of semiconductor circuits.

The smaller the atomic number of the element constituted of the material, the lower X-ray absorptivity the material has. Thus, the X-ray image of living soft tissue, soft material, or the like, cannot have sufficient contrast. Taking a case of an arthrosis of a human body as an example, both of cartilage and joint fluid surrounding the cartilage have water as a predominant ingredient, and little difference in the X-ray absorptivity therebetween. Thus, the X-ray image of the arthrosis hardly has sufficient contrast.

With this problem as a backdrop, X-ray phase imaging is actively researched in recent years. In the X-ray phase imaging, an image (hereinafter called phase contrast image) is obtained based on phase shifts (shifts in angle) of the X-rays that have passed through the object, instead of intensity distribution of the X-rays having passed therethrough. It is generally known that when the X-rays are incident upon the object, the phases of the X-rays interact with the material more closely than the intensity of the X-rays. Accordingly, the X-ray phase imaging, which takes advantage of phase difference, allows obtainment of the image with high contrast, even in capturing the image of the object constituted of the materials that have little difference in the X-ray absorptivity. As a type of the X-ray phase imaging, an X-ray imaging system using an X-ray Talbot interferometer, which is constituted of the X-ray source, two transmission diffraction gratings, and the X-ray image detector, is devised in recent years (refer to Japanese Patent Laid-Open Publication No. 2008-200360 and Applied Physics Letters, Vol. 81, No. 17, page 3287, written on October 2002 by C. David et al., for example).

The X-ray Talbot interferometer is constituted of the X-ray source, the X-ray image detector, and first and second diffraction gratings disposed between the X-ray source and the X-ray image detector. The second diffraction grating is disposed downstream from the first diffraction grating by a Talbot distance, which is determined from a grating pitch of the first diffraction grating and the wavelength of the X-rays. The Talbot distance is a distance at which the X-rays that have passed through the first diffraction grating form a self image by the Talbot effect. This self image is distorted and deformed according to the phase shifts of the X-rays due to passage through the object. By overlaying the second diffraction grating on the deformed self image of the first diffraction grating, i.e. by intensity modulation of the self image, moiré fringes appear.

The X-ray Talbot interferometer detects the moiré fringes by a fringe scanning technique. The phase contrast image of the object is obtained from change of the moiré fringes by the object. In the fringe scanning technique, a plurality of images are captured, while the second diffraction grating is slid relative to the first diffraction grating in a direction substantially parallel to a surface and orthogonal to a grating direction of the first diffraction grating at a scan pitch, which corresponds to an equally divided part of a grating pitch. By this scanning operation, the X-ray image detector detects periodic change in the intensity of pixel data of each pixel. From a phase shift amount (a phase shift amount between the presence and the absence of the object) of the periodic change in the intensity, a differential phase image (corresponding to angular distribution of the X-rays refracted by the object) is obtained. Integration of the differential phase image along a fringe scanning direction allows obtainment of the phase contrast image. Since the pixel data is a signal the intensity of which is periodically modulated in the scanning operation, a set of the pixel data obtained by the scanning operation is hereinafter called "intensity modulation signal". This fringe scanning technique is also adopted in an imaging system using laser light instead of the X-rays (refer to Applied Optics, Vol. 37, No. 26, page 6227, written on September 1998 by Hector Canabal et al.).

The X-ray imaging system using the X-ray Talbot interferometer requires high alignment accuracy between the first and second diffraction gratings, and tolerance for positional deviation in the grating direction (fringe scanning direction) is extremely small. Japanese Patent Laid-Open Publication No. 2008-200360 proposes to detect a positional deviation amount between the first and second diffraction gratings by an accelerometer and a position sensor, and to make a notification if the positional deviation amount is out of predetermined bounds.

However, the Japanese Patent Laid-Open Publication No. 2008-200360 needs provision of the accelerometer and the position sensor for detecting the positional deviation amount between the first and second diffraction gratings, and moreover needs provision of controllers for the accelerometer and the position sensor. Thus, the X-ray imaging system becomes complicated and expensive.

The Japanese Patent Laid-Open Publication No. 2008-200360 describes that above imaging operation is carried out without disposing the object between the X-ray source and the X-ray image detector, to calculate an offset amount $\Delta(x, y)$ of the differential phase image caused by a positional error between the first and second diffraction gratings and the like. However, the patent document does not describe to detect the positional deviation amount between the first and second diffraction gratings from the offset amount $\Delta(x, y)$. Also, when the positional deviation amount is large, the contrast of the intensity modulation signal is reduced. Thus, it becomes difficult to precisely calculate the positional deviation amount from the offset amount Δ(x, y).

Furthermore, the Japanese Patent Laid-Open Publication No. 2008-200360 aims to detect the positional deviation between the first and second diffraction gratings that occurs during application of the X-rays. The document does not describe the detection of the positional deviation due to time degradation.

SUMMARY OF THE INVENTION

An object of the present invention is to easily and precisely detect positional deviation between gratings due to time degradation, in a radiation imaging system for carrying out phase imaging with the use of the gratings.

To achieve the above and other objects, a radiation imaging system according to the present invention includes a first grating, an intensity modulator, a radiation image detector, an image processor, and a positional deviation detector. The first grating passes radiation emitted from a radiation source and produces a first fringe image. The intensity modulator provides intensity modulation to the first fringe image and produces a second fringe image in each of plural relative positions out of phase with one another with respect to a periodic pattern of the first fringe image. The radiation image detector detects the second fringe image. The image processor produces a phase contrast image of an object disposed between the radiation source and the radiation image detector based on a plurality of the second fringe images detected by the radiation image detector. The positional deviation detector detects a positional deviation between the first grating and the intensity modulator. The positional deviation detector obtains an intensity modulation signal from the plural second fringe images on a pixel-by-pixel basis, and evaluates the positional deviation based on a characteristic value of the intensity modulation signal.

The characteristic value may be an amplitude, a maximum value, a variance, or a standard deviation.

The positional deviation detector may compare a measurement of the characteristic value with a predetermined threshold value, and evaluate the positional deviation based on a comparison result. The positional deviation detector may include a notification section for making a notification about an evaluation result, or send the evaluation result to outside through a network.

The radiation imaging system may further include a source grating disposed between the radiation source and the first grating.

The intensity modulator may include a second grating and a scan mechanism. The second grating has a periodic pattern oriented in the same direction as that of the first fringe image. The scan mechanism slides one of the first and second gratings at a predetermined scan pitch. Both of the first and second gratings may be absorption gratings, and the first grating projects to the second grating the first fringe image produced by passage of the radiation. Otherwise, the first grating is a phase grating. The first fringe image is a self image of the first grating produced by the Talbot effect, and the first grating projects the self image to the second grating.

The radiation image detector may have a plurality of pixels, and each of the pixels may include a conversion layer for converting the radiation into an electric charge, and a charge collection electrode for collecting the electric charge converted by the conversion layer. The charge collection electrode includes plural linear electrode groups. The plural linear electrode groups are arranged so as to have a periodic pattern oriented in the same direction as that of the first fringe image and so as to be out of phase with one another. The intensity modulator is the charge collection electrode.

The image processor may include a differential phase image generator and a phase contrast image generator. The differential phase image generator obtains the intensity modulation signal from the plural second fringe images on a pixel-by-pixel basis, and calculates a phase shift amount of the intensity modulation signal to produce a differential phase image. The phase contrast image generator integrates the differential phase image along a direction of the periodic pattern to produce a phase contrast image.

A method for detecting a positional deviation between the first grating and the intensity modulator in the radiation imaging system includes the steps of capturing the second fringe image by the radiation image detector, obtaining the intensity modulation signal from the captured second fringe images on a pixel-by-pixel basis, comparing the measurement of the characteristic value of the intensity modulation signal with the predetermined threshold value, and evaluating the positional deviation based on the comparison result.

According to the present invention, the positional deviation between the first grating and the intensity modulator is evaluated based on the characteristic value of the intensity modulation signal, which is obtained on a pixel-by-pixel basis from the plural fringe images captured by the radiation image detector. Thus, it is possible to easily and precisely detect the positional deviation due to time degradation.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

First Embodiment

Figure 1:
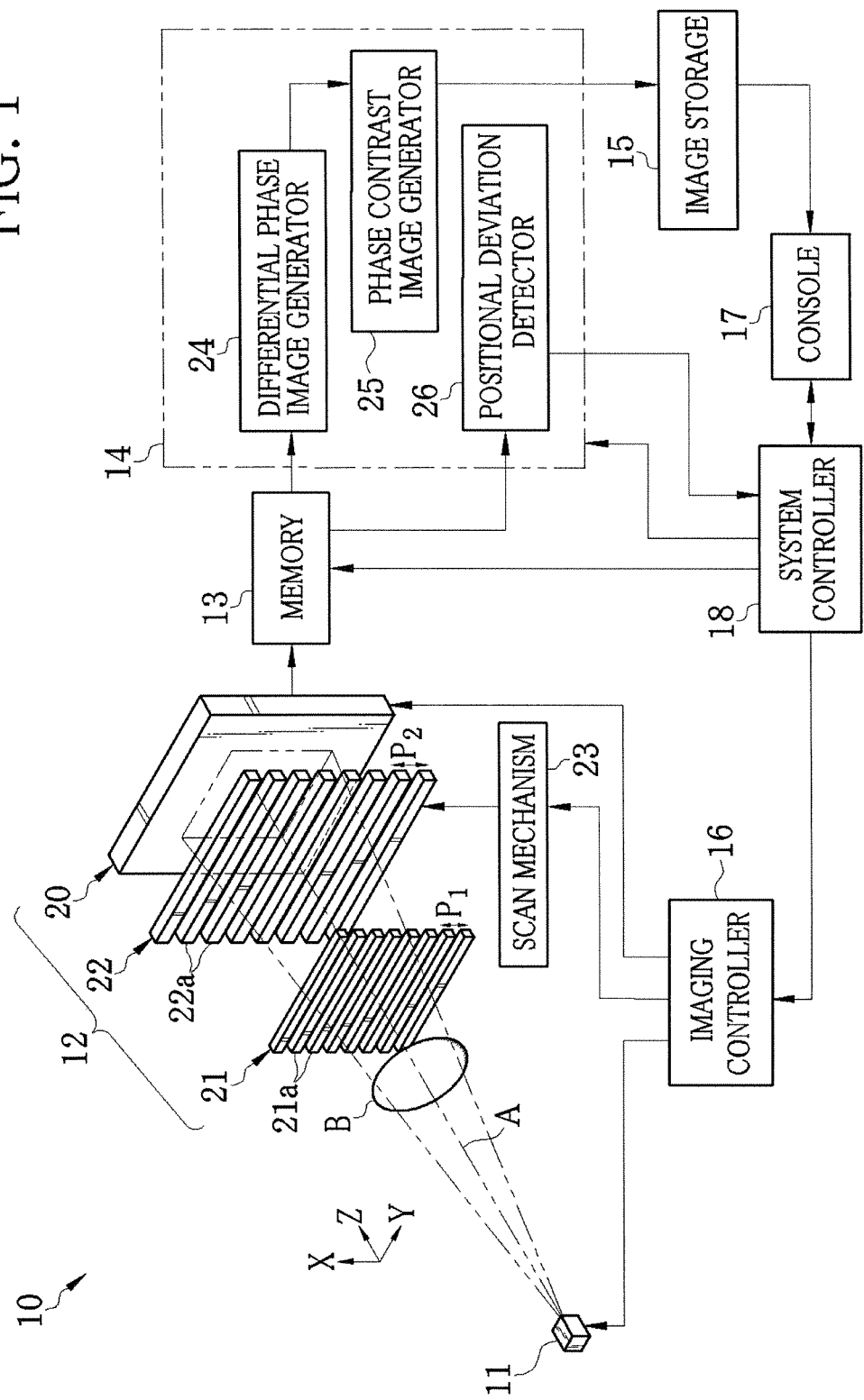
FIG. 1 is a schematic view of an X-ray imaging system according to a first embodiment.

As shown in FIG. 1, an X-ray imaging system 10 according to a first embodiment is constituted of an X-ray source 11 for emitting X-rays, an imaging unit 12, a memory 13, an image processor 14, an image storage 15, an imaging controller 16 for controlling the X-ray source 11 and the imaging unit 12, a console 17 including an operation unit and a monitor, and a system controller 18 for carrying out control of the entire X-ray imaging system 10 based on an operation signal inputted from the console 17. The imaging unit 12 is disposed so as to face the X-ray source 11, and detects the X-rays that have been emitted from the X-ray source 11 and passed through an object B, to produce image data. The memory 13 stores the image data outputted from the imaging unit 12. The image processor 14 produces a phase contrast image from plural frames of image data stored on the memory 13. The image storage 15 stores the phase contrast image produced by the image processor 14.

The X-ray source 11 is constituted of a high voltage generator, an X-ray tube, a collimator (all of them are not illustrated), and the like, and applies the X-rays to the object B under control of the imaging controller 16. The X-ray tube is, for example, a rotating anode X-ray tube. In the X-ray tube, an electron beam is emitted from a filament in accordance with a voltage generated by the high voltage generator, and collides with an anode rotating at a predetermined speed to generate the X-rays. The anode rotates for the purpose of reducing deterioration caused that the electron beam keeps colliding with the same point on the anode. A point with which the electron beam collides is referred to as an X-ray focus from which the X-rays radiate. The collimator restricts an irradiation field of the X-rays emitted from the X-ray tube, so as to block part of the X-rays outside an examination region of the object 13.

The imaging unit 12 includes a flat panel detector (FPD) 20 having semiconductor circuits, and first and second absorption gratings 21 and 22 that are used in detecting phase shifts (shifts in angle) of the X-rays caused by the object B to carry out phase imaging. The FPD 20 is disposed in such a position that a detection plane intersects at right angles with a direction (hereinafter called Z direction) along an optical axis A of the X-rays emitted from the X-ray source 11.

In the first absorption grating 21, a plurality of X-ray shield members 21a extending in a direction (hereinafter called Y direction) defined in a plane orthogonal to the Z direction are arranged in a direction (hereinafter called X direction) orthogonal to the Z and Y directions at a predetermined grating pitch $P_1$. In the second absorption grating 22, in a like manner, a plurality of X-ray shield members 22a extending in the Y direction are arranged in the X direction at a predetermined grating pitch $P_2$. The X-ray shield members 21a and 22a are preferably made of metal having high X-ray absorptivity, such as gold or lead.

The imaging unit 12 is provided with a scan mechanism 23 that slides one of the first and second absorption gratings 21 and 22 in the X direction to vary the relative position between the first and second absorption gratings 21 and 22. The scan mechanism 23 is constituted of an actuator such as a piezoelectric element, for example. The scan mechanism 23 is driven under the control of the imaging controller 16 during fringe scanning described later on. The memory 13 stores the plural frames of image data obtained by the imaging unit 12 in each scan step of the fringe scanning by the imaging unit 12. The second absorption grating 22 and the scan mechanism 23 compose an intensity modulator, as details will be described later on.

The image processor 14 includes a differential phase image generator 24 and a phase contrast image generator 25. The differential phase image generator 24 generates a differential phase image from the plural frames of image data, each frame of which is captured in one scan step of the fringe scanning by the FPD 20 and stored on the memory 13. The phase contrast image generator 25 generates a phase contrast image by integration of the differential phase image generated by the differential phase image generator 24 along the X direction. The phase contrast image generated by the phase contrast image generator 25 is written to the image storage 15, and then is outputted to the console 17 to be displayed on the monitor (not illustrated).

The image processor 14 is provided with a positional deviation detector 26 that detects the degree of positional deviation of the first and second absorption gratings 21 and 22 from a correct position, based on the plural frames of image data obtained in calibration operation by the FPD 20. In the calibration operation, the above fringe scanning is carried out in a state of the absence of the object B between the X-ray source 11 and the imaging unit 12, and the image data captured by the FPD 20 in each scan step is written to the memory 13, as details will be described later on. The positional deviation detector 26 evaluates the positional deviation based on a characteristic value (for example, amplitude value) of an intensity modulation signal obtained on a pixel-by-pixel basis.

The console 17 is provided with an input device (not illustrated) on which various types of commands are inputted, in addition to the monitor. The input device includes, for example, a switch, a touch panel, a mouse, and a key board. Operation on the input device allows input of X-ray imaging conditions such as the voltage of the X-ray tube and X-ray emission time, imaging timing, and the like. The monitor is a liquid crystal display or CRT display, and displays a menu of the X-ray imaging conditions and the above phase contrast image. Operation on the input device of the console 17 also allows execution of the calibration operation.

Figure 2:
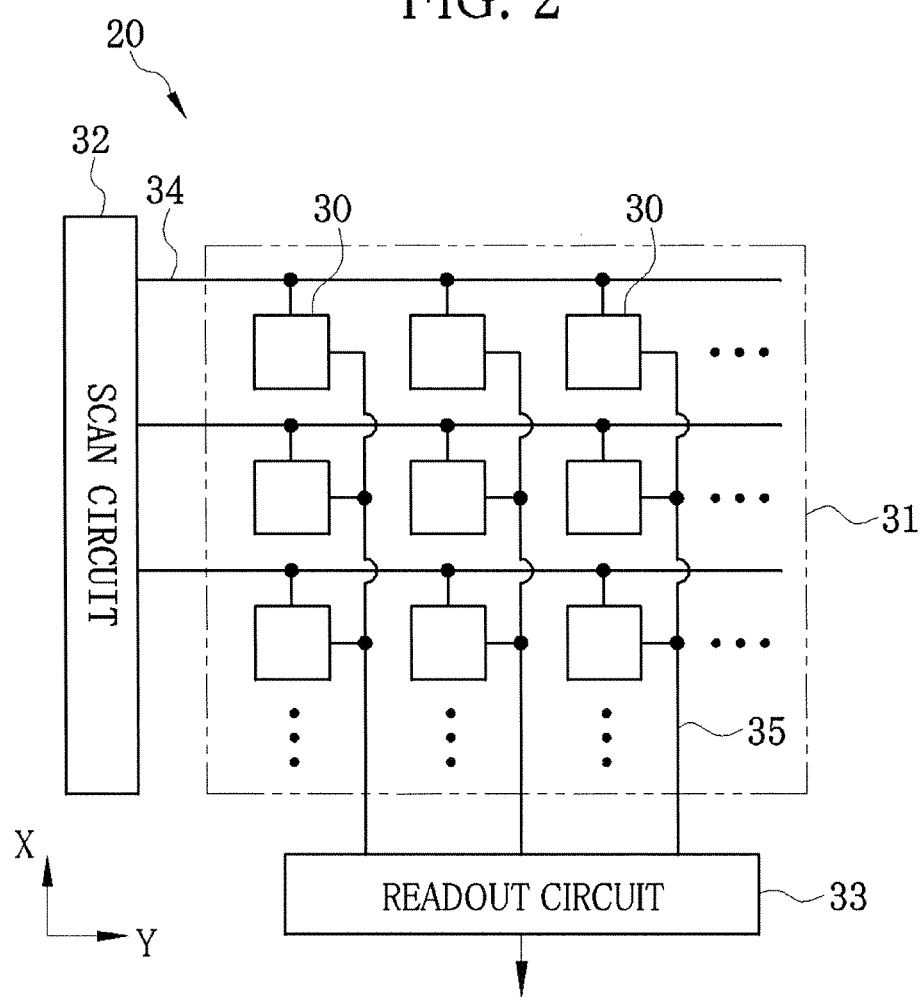
FIG. 2 is a schematic view of a flat panel detector.

As shown in FIG. 2, the FPD 20 is constituted of an imaging section 31, a scan circuit 32, and a readout circuit 33. The imaging section 31 has a plurality of pixels 30 arranged in two dimensions along the X and Y directions on an active matrix substrate. Each of the pixels 30 converts the X-rays into an electric charge and accumulates the electric charge. The scan circuit 32 controls readout timing of the electric charges from the imaging section 31. The readout circuit 33 reads out the electric charge accumulated in each pixel 30. The readout circuit 33 converts the electric charges into the image data, and writes the image data to the memory 13. The scan circuit 32 is connected to every pixel 30 by scan lines 34 on a line basis. The readout circuit 33 is connected to every pixel 30 by signal lines 35 on a column basis. The pixels 30 are arranged at a pitch of approximately 100 μm in each of the X and Y directions.

Each pixel 30 is a direct conversion type X-ray detecting element, in which a conversion layer (not illustrated) made of amorphous selenium or the like directly converts the X-rays into the electric charge, and the converted electric charge is accumulated in a capacitor (not illustrated) that is connected to an electrode below the conversion layer. To each pixel 30, a TFT switch (not illustrated) is connected. A gate electrode of the TFT switch is connected to the scan line 34, and a source electrode thereof is connected to the capacitor, and a drain electrode thereof is connected to the signal line 35. Upon turning on the TFT switch by a drive pulse from the scan circuit 32, the electric charge accumulated in the capacitor is read out to the signal line 35.

Each pixel 30 may be an indirect conversion type X-ray detecting element, in which a scintillator (not illustrated) made of gadolinium oxide ($Gd_2O_3$), cesium iodide (CsI), or the like converts the X-rays into visible light, and a photodiode (not illustrated) converts the visible light into the electric charge. In this embodiment, the FPD based on a TFT panel is used as a radiation image detector, but various types of radiation image detectors based on a solid-state image sensor such as a CCD image sensor and a CMOS image sensor may be used instead.

The readout circuit 33 includes an integrating amplifier, a correction circuit, an A/D converter (all of them are not illustrated), and the like. The integrating amplifier integrates the electric charge outputted from each pixel 30 through the signal line 35, to convert the electric charge into a voltage signal (image signal). The A/D converter converts the image signal produced by the integrating amplifier into digital image data. The correction circuit applies offset correction, gain correction, linearity correction, and the like to the image data, and writes the corrected image data to the memory 13.

Figure 3:
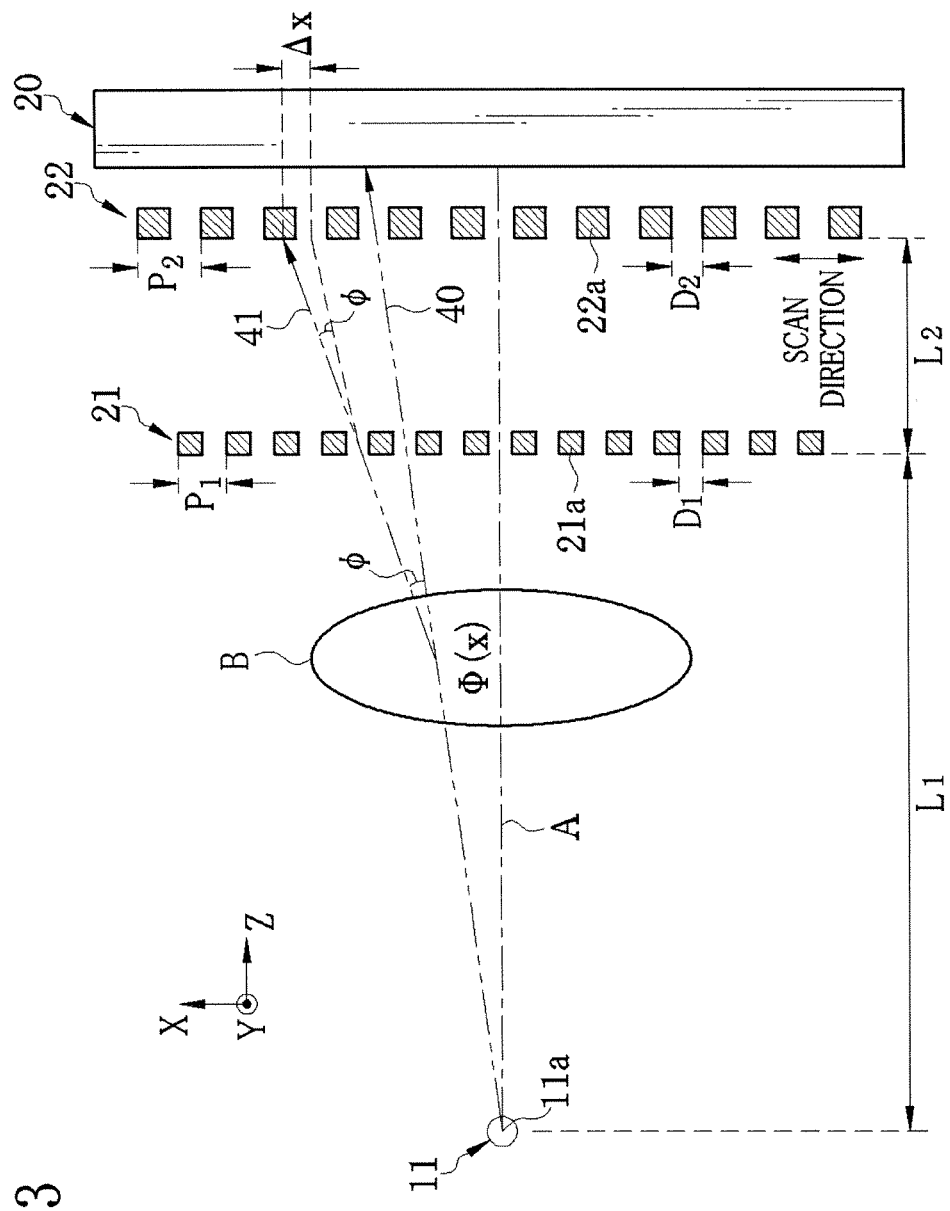
FIG. 3 is an explanatory view showing an example of difference in an X-ray path between the presence and the absence of an object.

In FIG. 3, the X-ray shield members 21*a* of the first absorption grating 21 are arranged in the X direction at the predetermined grating pitch $P_1$ and at a predetermined spacing distance $D_1$ apart from one another. The X-ray shield members 22*a* of the second absorption grating 22 are arranged in the X direction at the predetermined grating pitch $P_2$ and at a predetermined spacing distance $D_2$ apart from one another. The X-ray shield members 21*a* are arranged on an X-ray transparent substrate (not illustrated) such as a glass substrate, and the X-ray shield members 22*a* are arranged on an X-ray transparent substrate (not illustrated) such as a glass substrate, in a like manner. The first and second absorption gratings 21 and 22 provide the incident X-rays not with phase difference but with intensity difference. Thus, the first and second absorption gratings 21 and 22 are referred to as amplitude gratings. Slits (regions of the spacing distances $D_1$ and $D_2$) may not be clearances, but may be filled with an X-ray low-absorbent material such as a high polymer and light metal.

Irrespective of the presence or absence of the Talbot effect, the first and second absorption gratings 21 and 22 are designed so as to linearly project the X-rays having passed through the slits. To be more specific, the spacing distances $D_1$ and $D_2$ are set sufficiently larger than a peak wavelength of the X-rays emitted from the X-ray source 11, so that the X-rays applied to the slits are not diffracted but pass therethrough straight ahead. In a case where tungsten is used as the rotating anode of the X-ray tube and the voltage of the X-ray tube is 50 kV, for example, the peak wavelength of the X-rays is approximately 0.4 Å. In this case, if the spacing distances $D_1$ and $D_2$ are set at the order of 1 μm to 10 μm, almost all of the X-rays are linearly projected through the slits without diffraction. In this case, the grating pitches $P_1$ and $P_2$ are set at the order of 2 μm to 20 μm.

The X-rays emitted from the X-ray source 11 do not form a parallel beam, but form a cone beam radiating from the X-ray focus 11*a*. Thus, a projective image (hereinafter called G1 image or fringe image) projected through the first absorption grating 21 is magnified in proportion to a distance from the X-ray focus 11*a*. The grating pitch $P_2$ and the spacing distance $D_2$ of the second absorption grating 22 are designed so that the slits of the second absorption grating 22 substantially coincide with a periodic pattern of bright portions of the G1 image formed in the position of the second grating 22. In other words, the grating pitch $P_2$ and the spacing distance $D_2$ of the second absorption grating 22 satisfy the following expressions (1) and (2):

$$P_2 = \frac{L_1 + L_2}{L_1} P_1 \quad (1)$$

$$D_2 = \frac{L_1 + L_2}{L_1} D_1 \quad (2)$$

Wherein, $L_1$ represents a length from the X-ray focus 11*a* to the first absorption grating 21, and $L_2$ represents a length from the first absorption grating 21 to the second absorption grating 22.

In the case of the Talbot interferometer, the length $L_2$ between the first and second absorption gratings 21 and 22 is restricted to a Talbot distance, which depends on the grating pitch of the first diffraction grating and the wavelength of the X-rays. According to the imaging unit 12 of this embodiment, however, since the incident X-rays are projected through the first absorption grating 21 without diffraction, the G1 image of the first absorption grating 21 is observable in any position behind the first absorption grating 21 in a geometrically similar manner. Thus, the length $L_2$ between the first and second absorption gratings 21 and 22 can be established irrespective of the Talbot distance.

Although the imaging unit 12 according to this embodiment does not compose the Talbot interferometer, as described above, a Talbot distance Z is represented by the following expression (3), if the assumption is made that the first absorption grating 21 diffracts the X-rays and produces the Talbot effect:

$$Z = m \frac{P_1 P_2}{\lambda} \quad (3)$$

Wherein, λ represents the wavelength (peak wavelength) of the X-rays, and m represents a positive integer.

The expression (3) represents the Talbot distance when the X-rays emitted from the X-ray source 11 form the cone beam, and is known by Japanese Journal of Applied Physics, Vol. 47, No. 10, page 8077, written on October 2008 by Atsushi Momose et al.

In this embodiment, since the length $L_2$ can be established irrespective of the Talbot distance, as described above, the length $L_2$ is set shorter than the minimum Talbot distance Z defined at m=1, for the purpose of downsizing the imaging unit 12 in the Z direction. In other words, the length $L_2$ satisfies the following expression (4):

$$L_2 < \frac{P_1 P_2}{\lambda} \quad (4)$$

To produce a periodic pattern image with high contrast, it is preferable that the X-ray shield members 21*a* and 22*a* completely block (absorb) the X-rays. However, some of the X-rays pass through the X-ray shield members 21*a* and 22*a* without being absorbed, even with the use of the above material having high X-ray absorptivity (gold, lead, or the like). For this reason, it is preferable to thicken each of the X-ray shield members 21*a* and 22*a* (thickness in the Z direction) as much as possible (in other words, increase an aspect ratio of each shield member 21*a*, 22*a*), to increase X-ray shielding ability. For example, when the voltage of the X-ray tube is 50 kV, it is preferable to block 90% or more of the applied X-rays. In this case, the thickness of each X-ray shield member 21*a*, 22*a* is preferably 30 μm or more on a gold (Au) basis.

The FPD 20 captures a fringe image the intensity of which is modulated by superimposing the second absorption grating 22 on the G1 image of the first absorption grating 21. There is a slight deviation between a pattern period of the G1 image formed in the position of the second absorption grating 22 and the grating pitch $P_2$ of the second absorption grating 22 due to a manufacturing error and a placement error. This slight deviation causes moiré fringes appearing in the intensity-modulated fringe image.

If the object B is disposed between the X-ray source 11 and the first absorption grating 21, the FPD 20 detects the fringe image distorted or deformed by the object B. This deformation amount is proportional to an angle of each X-ray refracted by the object B. Consequently, analysis of the fringe image detected by the FPD 20 allows production of the phase contrast image of the object B.

Next, a method for analyzing the fringe image will be described. FIG. 3 shows an X-ray path 40 of one of the X-rays in the absence of the object B, and an X-ray path 41 of this X-ray in the presence of the object B. In the absence of the object B, the X-ray traveling in the X-ray path 40 passes through the first and second absorption gratings 21 and 22, and is incident upon the FPD 20. In the presence of the object B, on the other hand, the X-ray path 41 is refracted in accordance with phase shift distribution $\Phi(x)$ of the object B along the X direction. The X-ray traveling in the X-ray path 41 passes through the first absorption grating 21, and then is blocked by the X-ray shield member 22a of the second absorption grating 22. Likewise, in the absence of the object B, almost all of the X-rays that have passed through the first absorption grating 21 pass through the second absorption grating 22, because the first and second absorption gratings 21 and 22 are designed so as to satisfy the above expressions (1) and (2). In the presence of the object B, however, the X-ray is refracted by the object B at a refraction angle $\phi$. Thus, some of the X-rays that have passed through the first absorption grating 21 cannot pass through the second absorption grating 22.

When z represents a direction that the X-rays travel, the phase shift distribution $\Phi(x)$ of the object B is represented by the following expression (5):

$$\Phi(x) = \frac{2\pi}{\lambda} \int [1 - n(x, z)] dz \qquad (5)$$

Wherein, n(x,z) represents refractive index distribution of the object B. For the sake of simplicity, a Y coordinate is omitted in the expression (5).

As shown in FIG. 3, when $\phi$ represents the refraction angle of the X-ray refracted by the object B along the X direction, a displacement amount $\Delta x$ by the refraction is approximately represented by the following expression (6), on condition that the refraction angle $\phi$ is sufficiently small:

$$\Delta x \approx L_2 \phi \qquad (6)$$

The refraction angle $\phi$ is represented by the following expression (7), with the use of the wavelength $\lambda$ of the X-ray and the phase shift distribution $\Phi(x)$ of the object B:

$$\phi = \frac{\lambda}{2\pi} \frac{\partial \Phi(x)}{\partial x} \qquad (7)$$

As is obvious from the above expressions, the displacement amount $\Delta x$ of the X-ray due to the refraction by the object B relates to the phase shift distribution $\Phi(x)$ of the object B. Furthermore, the displacement amount $\Delta x$ relates to a phase shift amount $\psi$ (shift amount in a phase of the intensity modulation signal of each pixel 30 between in the presence of the object B and in the absence of the object B) of the intensity modulation signal of each pixel 30 detected by the FPD 20, as is represented by the following expression (8):

$$\psi = \frac{2\pi}{P_2} \Delta x = \frac{2\pi}{P_2} L_2 \phi \qquad (8)$$

Thus, the refraction angle $\phi$ is determined from the expression (8) and the phase shift amount $\psi$ of the intensity modulation signal of each pixel 30, and the differentiation of the phase shift distribution $\Phi(x)$ is determined from the expression (7) and the refraction angle $\phi$. Integrating the differentiation with respect to x allows to obtain the phase shift distribution $\Phi(x)$ of the object B, that is, to produce the phase contrast image of the object B. In this embodiment, the above phase shift amount $\psi$ is obtained by a fringe scanning technique described below.

In the fringe scanning technique, one of the first and second absorption gratings 21 and 22 is slid relative to the other in a stepwise manner in the X direction, and the image is captured whenever the sliding is carried out. In other words, the image is captured, whenever changing a phase of a grating period of one of the first and second absorption gratings 21 and 22 against that of the other. In this embodiment, the scan mechanism 23 described above slides the second absorption grating 22. With the sliding of the second absorption grating 22, the moiré fringes move. When a sliding distance (sliding amount in the X direction) reaches the single grating period (grating pitch $P_2$) of the second absorption grating 22 (in other words, the phase shift amount reaches $2\pi$, the moiré fringes return to the original positions. The FPD 20 captures the fringe images, while the second absorption grating 22 is slid at a scan pitch of an integer submultiple of the grating pitch $P_2$. Then, the intensity modulation signal of each pixel 30 is obtained from the captured plural fringe images. The differential phase image generator 24 of the image processor 14 applies arithmetic processing to the intensity modulation signal, to obtain the phase shift amount $\psi$ of the intensity modulation signal of each pixel 30.

Figure 4:
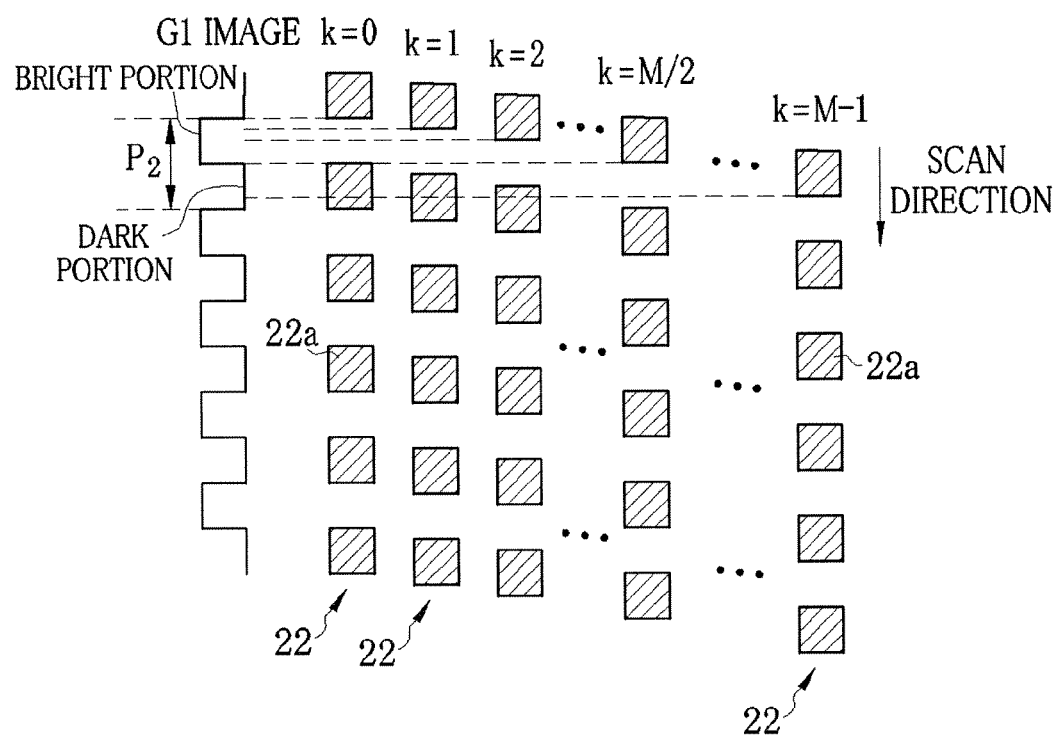
FIG. 4 is an explanatory view of a fringe scanning technique.

FIG. 4 schematically shows a state of shifting the second absorption grating 22 by a scan pitch of $P_2/M$, which the grating pitch $P_2$ is divided by M (integer of 2 or more). The scan mechanism 23 slides the second absorption grating 22 in a stepwise manner to each of an M number of scan positions represented by k=0, 1, 2, ..., M−1. According to FIG. 4, an initial position of the second absorption grating 22 is defined as a position (k=0) in which the X-ray shield members 22a substantially coincide with dark portions of the G1 image formed in the position of the second absorption grating 22 in the absence of the object B. However, the initial position may be defined as any position out of k=0, 1, 2, ... M−1.

In the position of k=0, the X-rays to be detected through the second absorption grating 22 include a component (non-refracted X-ray component) of the X-rays that has not been refracted by the object B, and a part of a component (refracted X-ray component) of the X-rays that has been refracted by the object B and passed through the first absorption grating 21. While the second absorption grating 22 is successively slid to k=1, 2, ..., the non-refracted X-ray component is decreased and the refracted X-ray component is increased in the X-rays to be detected through the second absorption grating 22. Especially, in the position of k=M/2, substantially only the refracted X-ray component is detected through the second absorption grating 22. After the position of M/2, on the contrary, the refracted X-ray component is decreased and the non-refracted X-ray component is increased in the X-rays to be detected through the second absorption grating 22.

Since the FPD 20 captures the image in each of the positions of k=0, 1, 2, ..., M−1, an M number of pixel data is obtained on each pixel 30. A method for calculating the phase shift amount ψ of the intensity modulation signal of each pixel 30 from the M number of pixel data will be hereinafter described. When the second absorption grating 22 is in the position k, pixel data $I_k(x)$ of each pixel 30 is represented by the following expression (9):

$$I_k(x) = A_0 + \sum_{n>0} A_n \exp\left[2\pi i \frac{n}{P_2}\left\{L_2\phi(x) + \frac{kP_2}{M}\right\}\right] \quad (9)$$

Wherein, x represents a coordinate of the pixel in the X direction, and $A_0$ represents the intensity of the incident X-rays, and $A_n$ represents a value corresponding to contrast of the intensity modulation signal (n is a positive integer). φ(x) represents the refraction angle φ described above as a function of the coordinate x of the pixel 30.

With the use of the following expression (10), the refraction angle φ(x) is represented by the following expression (11):

$$\sum_{k=0}^{M-1} \exp\left(-2\pi i \frac{k}{M}\right) = 0 \quad (10)$$

$$\phi(x) = \frac{P_2}{2\pi L_2}\arg\left[\sum_{k=0}^{M-1} I_k(x)\exp\left(-2\pi i \frac{k}{M}\right)\right] \quad (11)$$

Wherein, "arg[ ]" means an argument of a complex number, and corresponds to the phase shift amount ψ of the intensity modulation signal of each pixel. Therefore, the determination of the phase shift amount ψ based on the expression (11) from the M number of pixel data (intensity modulation signals) obtained from each pixel 30 allows obtainment of the refraction angle φ(x) and the differentiation of the phase shift distribution Φ(x).

Figure 5:
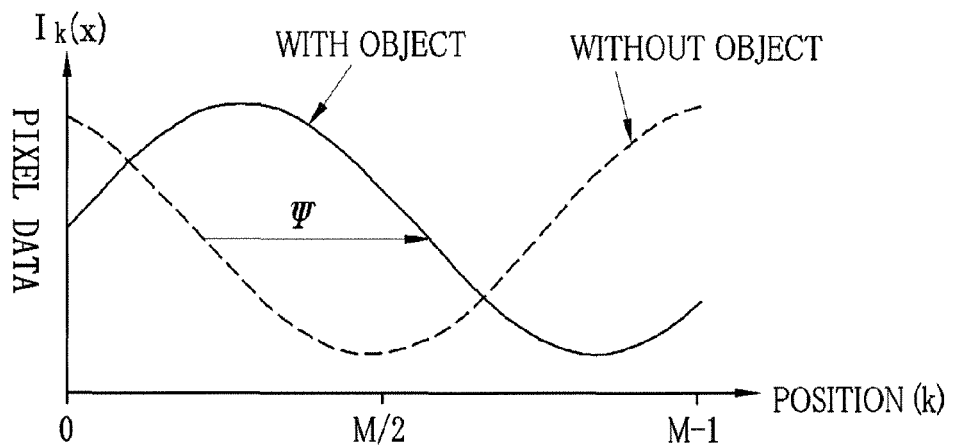
FIG. 5 is a graph of pixel data (intensity modulation signals) obtained by the fringe scanning technique.

To be more specific, as shown in FIG. 5, the M number of pixel data obtained from each pixel 30 periodically varies with a period of the grating pitch $P_2$ with respect to the position k of the second absorption grating 22. In FIG. 5, a dashed line represents a plot of the pixel data in the absence of the object B, and a solid line represents a plot of the pixel data in the presence of the object B. The phase difference between waveforms of both of the plots corresponds to the above phase shift amount ψ of the intensity modulation signal of each pixel.

Although a Y coordinate of each pixel 30 is not considered in the above description, carrying out similar calculations with respect to each Y coordinate allows obtainment of two-dimensional distribution ψ(x,y) of the phase shift amounts along the X and Y directions. This two-dimensional distribution ψ(x,y) of the phase shift amounts corresponds to the differential phase image.

This differential phase image is inputted to the phase contrast image generator 25. The phase contrast image generator 25 integrates the inputted differential phase image along an X axis, to obtain the phase shift distribution Φ(x,y) of the object B. The phase shift distribution Φ(x,y) is written to the image storage 15 as the phase contrast image.

Next, the detection of the positional deviation between the first and second absorption gratings 21 and 22 by the positional deviation detector 26 will be described. It is preferable that the position ($L_1$, $L_2$) of the first and second absorption gratings 21 and 22 in the Z direction is set so as to satisfy the above expressions (1) and (2). If the first and second absorption gratings 21 and 22 satisfy the above expressions (1) and (2), and do not deviate in the grating direction (X direction), an amplitude value (i.e. contrast) of the intensity modulation signal obtained by each pixel 30 is maximized.

If the position of at least one of the first and second absorption gratings 21 and 22 deviates in the Z or X direction, alignment accuracy between the G1 image of the first absorption grating 21 and the second absorption grating 22 is reduced in the fringe scanning, and hence the amplitude value of the intensity modulation signal is reduced. The reduction in the amplitude value can also occur, when the first and second absorption gratings 21 and 22 rotate (rotation about the X axis, rotation about a Y axis, rotation about a Z axis, or combined rotation thereof).

The above expression (9) represents the intensity modulation signal without the positional deviation between the first and second absorption gratings 21 and 22. In the presence of the positional deviation between the first and second absorption gratings 21 and 22, the intensity modulation signal is represented by the following expression (12):

$$I_k(x) = A_0 + \sum_{n>0}(A_n + \delta_n)\exp\left[2\pi i \frac{n}{P_2}\left\{L_2\phi(x) + \Delta(x) + \frac{kP_2}{M}\right\}\right] \quad (12)$$

Figure 6:
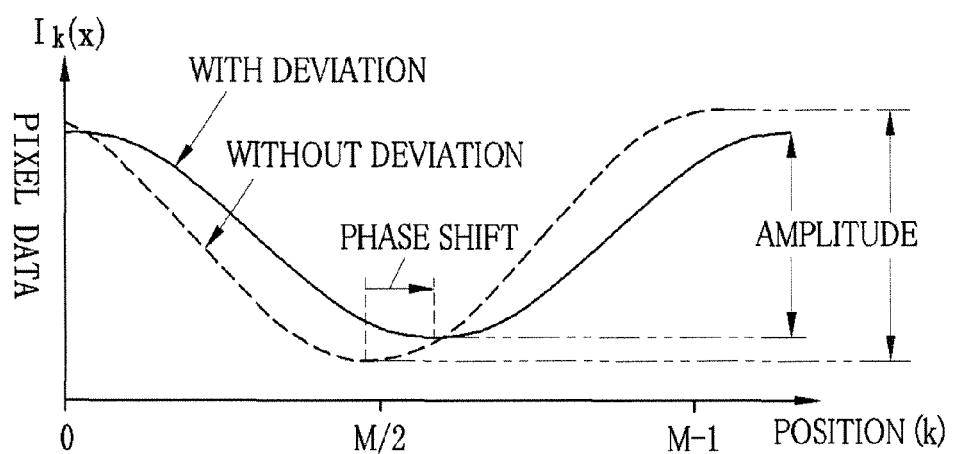
FIG. 6 is a graph for explaining change in the intensity modulation signal caused by positional deviation between first and second absorption gratings.

Wherein, $\delta_n$ corresponds to variation in the amplitude value (contrast) of the intensity modulation signal due to the positional deviation. Δ(x) corresponds to the phase shift amount of the intensity modulation signal due to the positional deviation (see FIG. 6).

The positional deviation detector 26 calculates the amplitude value of the intensity modulation signal obtained by each pixel 30, and compares the calculated amplitude value with a predetermined threshold value to evaluate the positional deviation. The amplitude value is obtained by calculating a difference between a maximum value and a minimum value of the pixel data $I_k(x)$ obtained in each scan position k. If the amplitude value cannot be obtained from the maximum and minimum values of the pixel data $I_k(x)$ because of shortage in the number of the scan positions k, a sine wave that is best fit for the obtained pixel data $I_k(X)$ is determined, and the amplitude value of the sine wave is obtained.

The positional deviation detector 26 uses the first and second threshold values. For example, the first threshold value corresponds to a value 25% lower than the amplitude value without the positional deviation. For example, the second threshold value corresponds to a value 50% lower than the amplitude value without the positional deviation.

If the amplitude value of the intensity modulation signal of at least one pixel 30 is less than the first threshold value, the positional deviation detector 26 sends a warning signal to the system controller 18. If the amplitude value of the intensity modulation signal of at least one pixel 30 is less than the second threshold value, the positional deviation detector 26 sends an error signal to the system controller 18.

Upon receiving the warning or error signal from the positional deviation detector 26, the system controller 18 displays a message (warning message or error message) corresponding to the received signal on the monitor of the console 17. Thus, an operator realizes the presence of the positional deviation between the first and second absorption gratings 21 and 22, and grasps the degree of reliability in image quality of the phase contrast image.

As described above, the positional deviation detector 26 evaluates the positional deviation based on the pixel 30 that has the smallest amplitude value of the intensity modulation signal. Thus, if there is a defective pixel that cannot produce the normal intensity modulation signal, a wrong evaluation is made, and the warning or error signal may be outputted irrespective of the positional deviation between the first and second absorption gratings 21 and 22. For this reason, it is preferable that the positional deviation detector 26 averages the amplitude values of the intensity modulation signals of all pixels 30 or a predetermined number of pixels 30, and compares this average value with the above first and second threshold values to evaluate the positional deviation.

Figure 7:
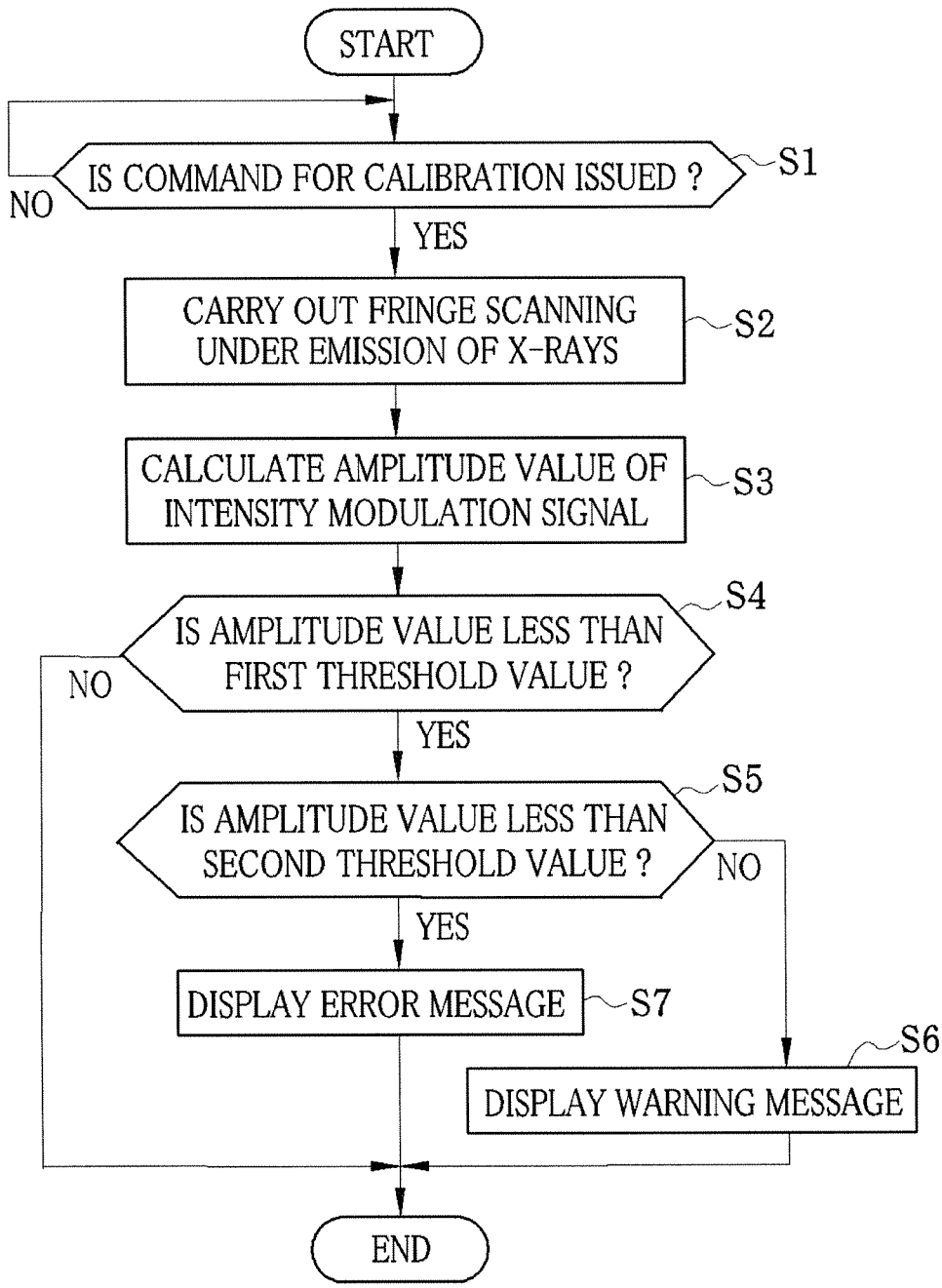
FIG. 7 is a flowchart of calibration operation.

The positional deviation detector 26 carries out an above evaluation procedure of the positional deviation during calibration operation, which is carried out in the absence of the object B between the X-ray source 11 and the imaging unit 12. The calibration operation will be described in detail with referring to a flowchart of FIG. 7.

When a command for calibration is inputted from the operation unit of the console (YES in S1), the system controller 18 commands the FPD 20 to carry out the imaging operation (fringe scanning operation) in each scan position, while the scan mechanism 23 slides the second absorption grating 22 to each of the scan positions of k=0, 1, 2, ..., M−1, in a state of emission of the X-rays of predetermined intensity from the X-ray source 11. The image data obtained in each scan position is written to the memory 13 (S2).

The plural frames of image data stored on the memory 13 are read out to the positional deviation detector 26. The positional deviation detector 26 calculates the amplitude value of the pixel data (intensity modulation signal) on a pixel-by-pixel basis (S3). Then, the positional deviation detector 26 compares at least one of the calculated amplitude values with the first threshold value (S4). If the amplitude value is the first threshold value or more (NO in S4), the evaluation procedure is ended.

If the amplitude value is less than the first threshold value (YES in S4), on the other hand, the positional deviation detector 26 compares the amplitude value with the second threshold value (S5). If the amplitude value is the second threshold value or more (NO in S5), the warning signal is sent to the system controller 18. In response to the warning signal, the warning message is displayed on the monitor (S6). If the amplitude value is less than the second threshold value (YES in S5), on the other hand, the error signal is sent to the system controller 18. In response to the error signal, the error message is displayed on the monitor (S7).

Figure 8:
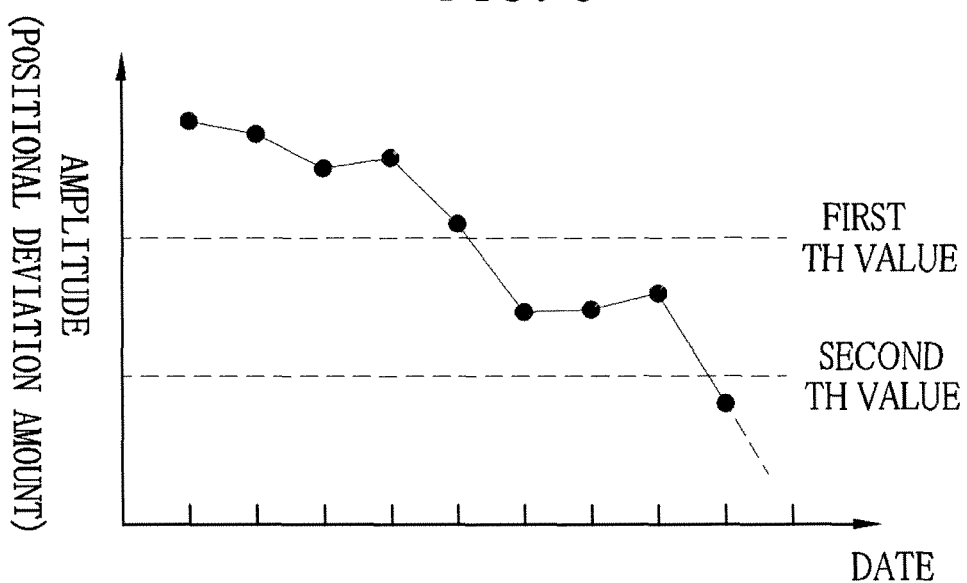
FIG. 8 is a graph showing an example of a history of an amplitude value of the intensity modulation signal.

It is preferable that the system controller 18 stores as a history a date of carrying out the calibration operation and the amplitude value in relation to each other, and produces and displays on the monitor a graph as shown in FIG. 8, whenever the calibration operation is ended. This facilitates a grasp of the history of the positional deviation between the first and second absorption gratings 21 and 22 at sight, and early investigation into a cause of the positional deviation, early correction of misalignment, and the like.

In this embodiment, to inform the operator of the positional deviation between the first and second absorption gratings 21 and 22, the warning or error message is displayed on the monitor in accordance with the degree of the positional deviation. However, the operator may be informed of the positional deviation by sound, lighting of a warning lamp, or the like.

In this embodiment, the two kinds of threshold values (first and second threshold values) are used to evaluate the degree of the positional deviation between the first and second absorption gratings 21 and 22, but the number and numerical values of the threshold values, variations of the messages, and the like are appropriately changeable.

In this embodiment, the amplitude value is used as the characteristic value of the intensity modulation signal to evaluate the degree of the positional deviation. However, a maximum value of the intensity modulation signal is usable instead of the amplitude value to evaluate the degree of the positional deviation, because the maximum value of the intensity modulation signal varies with the positional deviation between the first and second absorption gratings 21 and 22, just as with the amplitude value. Furthermore, a variance value or a standard deviation is usable as the characteristic value of the intensity modulation signal to evaluate the degree of the positional deviation. Since the variance value and the standard deviation represent the degree of variation of the intensity modulation signal with respect to an average value of the intensity modulation signal similarly to the amplitude value, the variance value and the standard deviation vary with the positional deviation.

Figure 9:
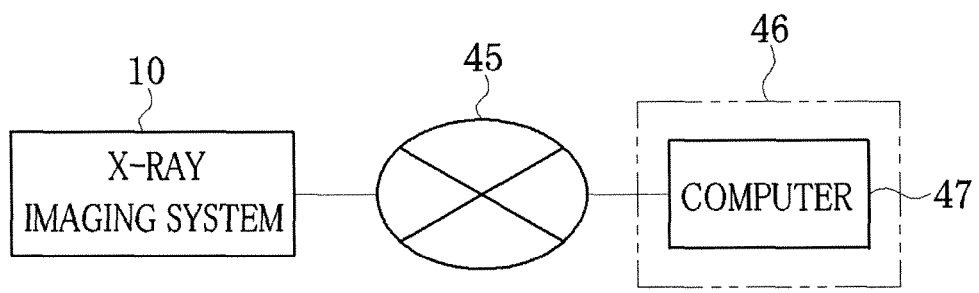
FIG. 9 is a schematic view of the X-ray imaging system connected to a service center through a network.

An evaluation result obtained by comparison between the amplitude value of the intensity modulation signal and the threshold values may not be sent to the console 17. As shown in FIG. 9, the X-ray imaging system 10 may be connected to a computer 47 of a service center 46 through a network 45 such as the Internet, and the evaluation result may be sent to the computer 47 through the network 45. This allows a staff of the service center 46 to monitor a state of the X-ray imaging system 10 at a distant location, and grasp and deal with a failure directly.

In this embodiment, the object B is disposed between the X-ray source 11 and the first absorption grating 21. However, even if the object B is disposed between the first and second absorption gratings 21 and 22, the phase contrast image can be produced in a like manner.

Second Embodiment

Figure 10:
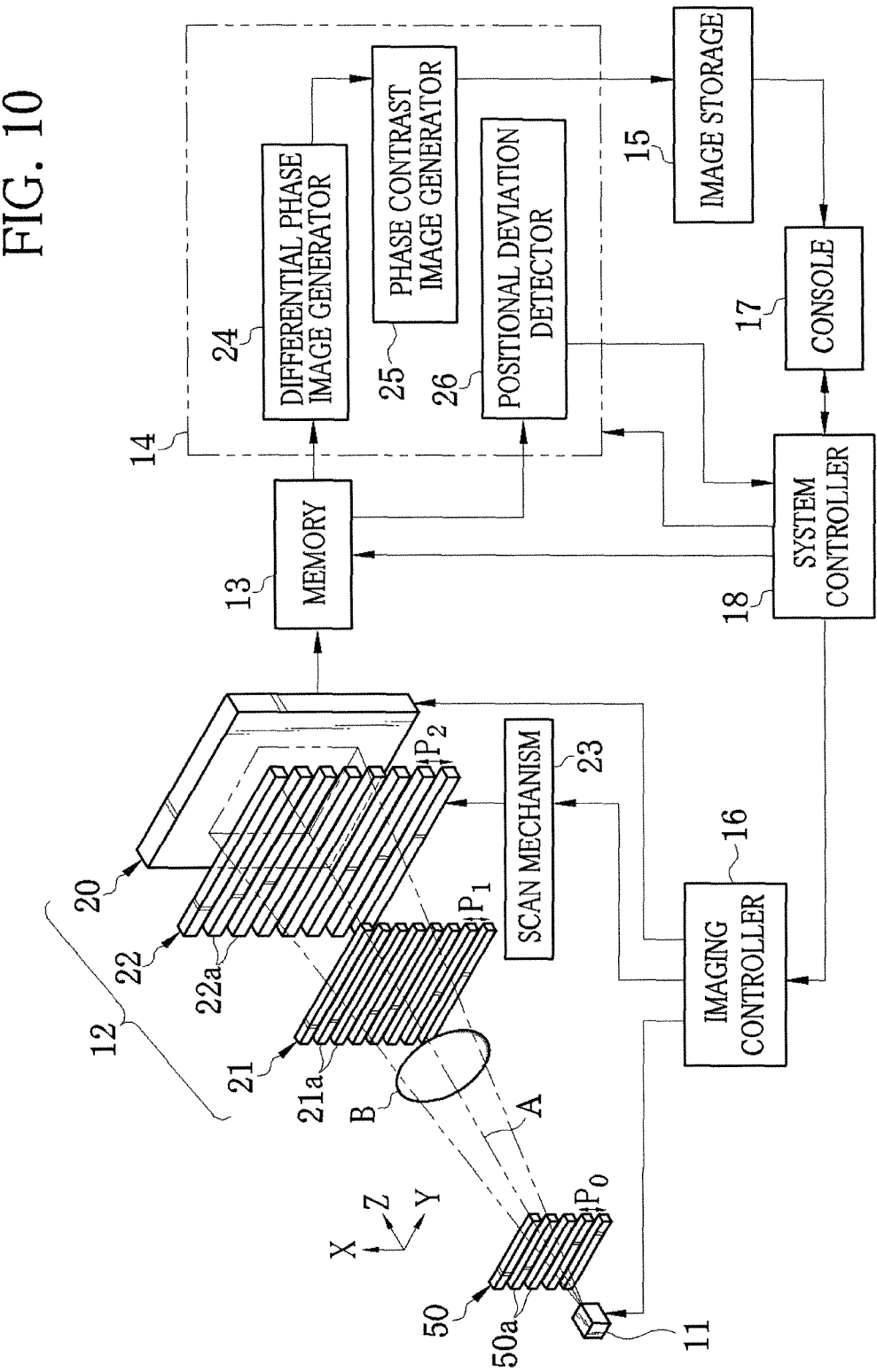
FIG. 10 is a schematic view of the X-ray imaging system according to a second embodiment.

In the above first embodiment, if the length from the X-ray source 11 to the FPD 20 is elongated, the G1 image is blurred due to a size (0.1 mm to 1 mm, in general) of the X-ray focus 11a. The blur causes degradation in the image quality of the phase contrast image. For this reason, a multi-slit (source grating) 50 may be disposed just behind the X-ray focus 11a, as shown in FIG. 10.

The multi-slit 50 is an absorption grating that is similar to the first and second absorption gratings 21 and 22. In the multi-slit 50, a plurality of X-ray shield members 50a extending in the Y direction are periodically arranged in the X direction at a predetermined grating pitch $P_0$. This multi-slit 50 partly blocks the X-rays emitted from the X-ray source 11 to reduce the effective focus size in the X direction, and forms a number of point sources (distributed light sources) in the X direction, in order to prevent the blur of the G1 image.

The grating pitch $P_0$ of the multi-slit 50 has to satisfy the following expression (13):

$$P_0 = \frac{L_0}{L_2} P_2 \tag{13}$$

Wherein, $L_0$ represents a length from the multi-slit 50 to the first absorption grating 21, and $L_2$ represents a length between the first and second absorption gratings 21 and 22.

In this embodiment, the position of the multi-slit 50 substantially becomes the position of the X-ray focus. Thus, the grating pitch $P_2$ and the spacing distance $D_2$ of the second absorption grating 22 are determined so as to satisfy the following expressions (14) and (15):

$$P_2 = \frac{L_0 + L_2}{L_0} P_1 \quad (14)$$

$$D_2 = \frac{L_0 + L_2}{L_0} D_1 \quad (15)$$

It is preferable that the multi-slit 50 and the first and second absorption gratings 21 and 22 are ideally disposed so as to satisfy the above expressions (13) to (15). If the positions of the multi-slit 50 and the first and second absorption gratings 21 and 22 deviate from one another, the characteristic value of the intensity modulation signal varies. Thus, in this embodiment, the positional deviation detector 26 can evaluate the positional deviation, as in the case of the first embodiment.

Third Embodiment

In the above first and second embodiments, the first and second absorption gratings 21 and 22 linearly project the X-rays that have passed through the slits. However, the present invention is applicable to a radiation imaging apparatus (refer to International Publication No. WO2004/058070) in which the slits diffract the X-rays to produce the so-called Talbot effect. In this case, however, the length $L_2$ between the first and second absorption gratings 21 and 22 has to be set at the Talbot distance. Also, in this case, a phase grating (phase diffraction grating) is usable instead of the first absorption grating 21. This phase grating projects to the second absorption grating 22 the fringe image (self image) produced by the Talbot effect.

The difference between the phase grating and the absorption grating is only the thickness of an X-ray absorptive material (X-ray shield members). The X-ray shield members of the absorption grating have a thickness of approximately 30 μm or more on an Au basis, while those of the phase grating have a thickness of 1 μm to 5 μm at most. In the phase grating, the X-ray absorptive material provides a predetermined amount ($\pi$ or $\pi/2$) of phase modulation to the X-rays emitted from the X-ray source 11, and causes the Talbot effect, to produce the fringe image being the self image.

As in the case of the first and second embodiments, it is preferable that the positional relation between the phase grating used instead of the first absorption grating 21 and the second absorption grating 22 satisfies the above expressions (1) and (2), in order to obtain the phase contrast image of high quality. Thus, in this embodiment, the positional deviation detector 26 can evaluate the positional deviation, as in the case of the first embodiment.

Fourth Embodiment

In the above first to third embodiments, the second absorption grating 22 is provided separately from the FPD 20. However, the use of an X-ray image detector disclosed in U.S. Pat. No. 7,746,981 eliminates the provision of the second absorption grating 22. This X-ray image detector being a direct conversion X-ray image detector is provided with a conversion layer for converting the X-rays into electric charges and charge collection electrodes for collecting the electric charges converted by the conversion layer. In each pixel, the charge collection electrode includes plural linear electrodes arranged at a regular period. The linear electrodes are grouped and electrically connected to compose linear electrode groups. The linear electrode groups are laid out so as to be regularly out of phase with one another. The charge collection electrodes correspond to the intensity modulator.

Figure 11:
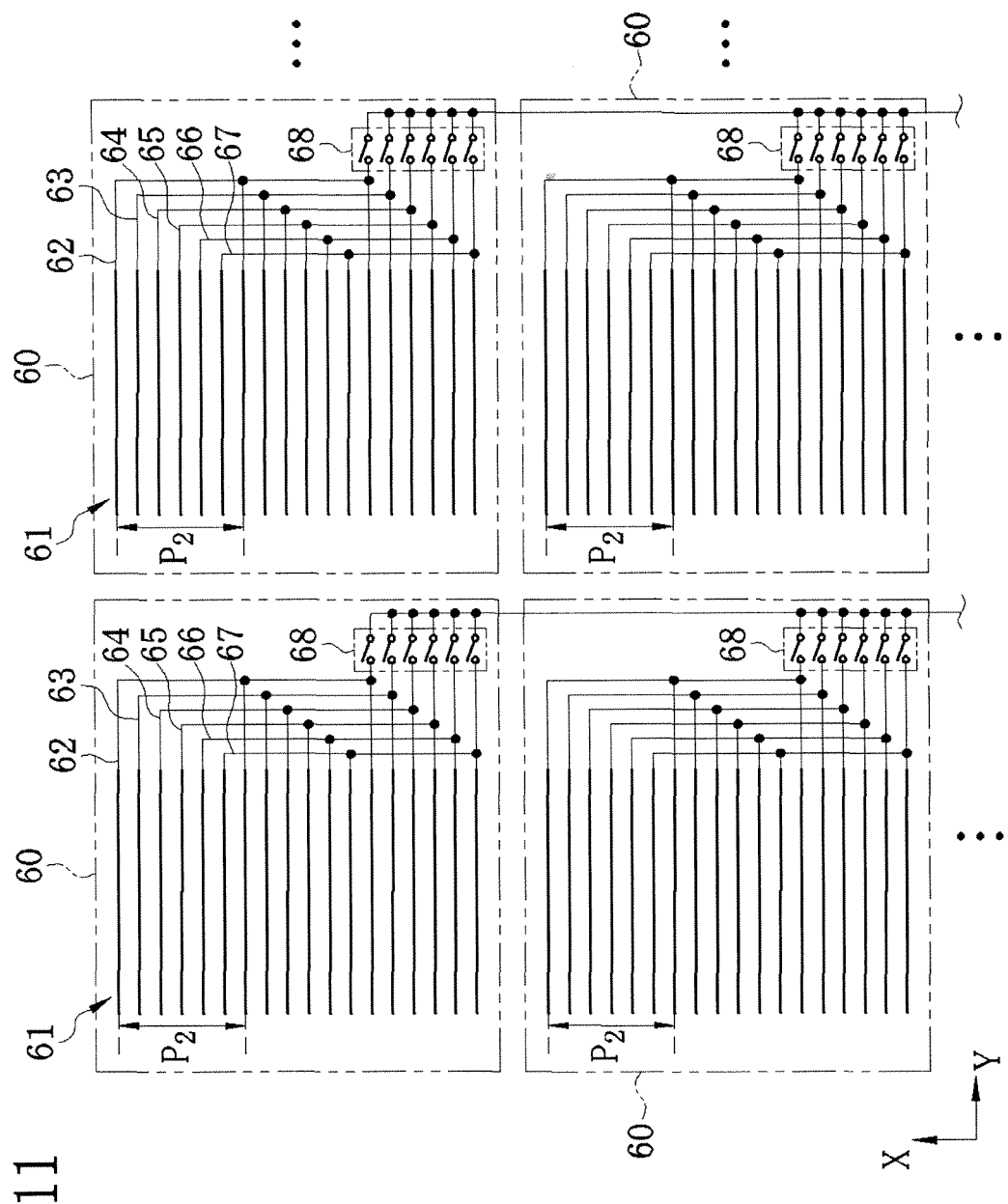
FIG. 11 is a schematic view of a part of an X-ray image detector according to a fourth embodiment.

FIG. 11 shows a FPD according to a fourth embodiment. In the FPD, pixels 60 are arranged in two dimensions along the X and Y directions at a constant arrangement pitch. In each of the pixels 60, a charge collection electrode 61 is formed to collect the electric charges converted by the conversion layer, which converts the X-rays into the electric charges. The charge collection electrode 61 includes first to sixth linear electrode groups 62 to 67. The first to sixth linear electrode groups 62 to 67 are arranged out of phase with one another by $\pi/3$. To be more specific, if the phase of the first linear electrode group 62 is zero, the phases of the second to sixth linear electrode groups 63 to 67 are set at $\pi/3$, $2\pi/3$, $\pi$, $4\pi/3$, $5\pi/3$, respectively.

Furthermore, the each pixel 60 is provided with a switch group 68 to read out the electric charges collected by the charge collection electrode 61. The switch group 68 includes TFT switches provided one by one for the one to sixth linear electrode groups 62 to 67. By controlling the switch group 68, the electric charges collected by the first to sixth linear electrode groups 62 to 67 are separately read out. Thus, it is possible to obtain six fringe images out of phase with one another in the single imaging operation, and to produce the phase contrast image based on the six fringe images.

The use of the above X-ray image detector instead of the FPD 20 eliminates the need for provision of the second absorption grating 22 in the imaging unit 12, and hence brings about reduction in cost and size. Also, in this embodiment, since the plural fringe images that are subjected to the intensity modulation in the different phases can be captured in the single imaging operation, it is possible to eliminate the need for carrying out physical scanning operation for the fringe scanning and provision of the scan mechanism 23 described above. Instead of the charge collection electrodes 61, other types of charge collection electrodes disclosed in the U.S. Pat. No. 7,746,981 are usable.

In this embodiment, the first absorption grating 21 is preferably disposed so as to satisfy the above expression (1), wherein $L_1$ represents the length from the X-ray source 11a to the first absorption grating 21, $L_2$ represents a length from the first absorption grating 21 to the X-ray image detector, and $P_2$ represents the arrangement pitch of the linear electrodes of the first to sixth linear electrode groups 62 to 67 in the X direction. Thus, in this embodiment, the positional deviation detector 26 can evaluate the positional deviation, as in the case of the first embodiment.

Furthermore, as another embodiment without the provision of the second absorption grating 22, the fringe image (G1 image) captured by the X-ray image detector may be periodically sampled in synchronization with change in the phase by signal processing, to modulate the intensity of the fringe image.

All of the above embodiments use the X-ray source 11 for emitting the X-rays of the cone beam, but may use an X-ray source for emitting parallel X-rays. In this case, the above expressions (1) to (4) are modified into the following expressions (16) to (19):

$$P_2 = P_1 \quad (16)$$

$$D_2 = D_1 \quad (17)$$

$$Z = m\frac{P_1^2}{\lambda} \quad (18)$$

$$L_2 < \frac{P_1^2}{\lambda} \quad (19)$$

Each of the embodiments described above is applicable to various types of radiation imaging systems for medical diagnosis, industrial use, nondestructive inspection, and the like. As the radiation, gamma rays or the like are usable other than the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An X-ray radiation imaging system comprising:
   a first grating for passing X-ray radiation emitted from an X-ray radiation source and producing a first fringe image;
   an intensity modulator for applying intensity modulation to the first fringe image and producing a second fringe image in each of plural relative positions out of phase with one another with respect to a periodic pattern of the first fringe image;
   an X-ray radiation image detector for detecting the second fringe image;
   an image processor for producing a phase contrast image of an object disposed between the X-ray radiation source and the X-ray radiation image detector based on a plurality of the second fringe images detected by the X-ray radiation image detector; and
   a positional deviation detector for detecting a positional deviation between the first grating and the intensity modulator, the positional deviation detector obtaining an intensity modulation signal from the plural second fringe images on a pixel-by-pixel basis, and evaluating the positional deviation based on a characteristic value of the intensity modulation signal.

2. The X-ray radiation imaging system according to claim 1, wherein the characteristic value comprises an amplitude, a maximum value, a variance, or a standard deviation.

3. The X-ray radiation imaging system according to claim 2, wherein the positional deviation detector compares a measurement of the characteristic value with a predetermined threshold value, and evaluates the positional deviation based on a comparison result, and the positional deviation detector includes a notification section for making a notification about an evaluation result.

4. The X-ray radiation imaging system according to claim 2, wherein the positional deviation detector compares a measurement of the characteristic value with a predetermined threshold value, and evaluates the positional deviation based on a comparison result, and sends an evaluation result to outside through a network.

5. The X-ray radiation imaging system according to claim 1, further comprising:
   a source grating disposed between the X-ray radiation source and the first grating.

6. The X-ray radiation imaging system according to claim 1, wherein the intensity modulator includes a second grating and a scan mechanism, and the second grating includes a periodic pattern oriented in a same direction as that of the first fringe image, and the scan mechanism slides one of the first and second gratings at a predetermined scan pitch.

7. The X-ray radiation imaging system according to claim 6, wherein both of the first and second gratings are absorption gratings, and the first grating projects to the second grating the first fringe image produced by passage of the X-ray radiation.

8. The X-ray radiation imaging system according to claim 6, wherein the first grating comprises a phase grating, and the first fringe image comprises a self image of the first grating produced by a Talbot effect, and the first grating projects the self image to the second grating.

9. The X-ray radiation imaging system according to claim 1,
   wherein the X-ray radiation image detector has a plurality of pixels, and each of the pixels includes a conversion layer for converting the X-ray radiation into an electric charge, and a charge collection electrode for collecting the electric charge converted by the conversion layer;
   wherein the charge collection electrode includes plural linear electrode groups, and the plural linear electrode groups are arranged so as to include a periodic pattern oriented in a same direction as that of the first fringe image and so as to be out of phase with one another; and
   wherein the intensity modulator comprises the charge collection electrode.

10. The X-ray radiation imaging system according to claim 1, wherein the image processor includes a differential phase image generator and a phase contrast image generator, and the differential phase image generator obtains the intensity modulation signal from the plural second fringe images on a pixel-by-pixel basis and calculates a phase shift amount of the intensity modulation signal to produce a differential phase image, and the phase contrast image generator integrates the differential phase image along a direction of the periodic pattern to produce a phase contrast image.

11. A method for detecting a positional deviation between a first grating and an intensity modulator in a X-ray radiation imaging system, the X-ray radiation imaging system including the first grating for passing X-ray radiation emitted from an X-ray radiation source and producing a first fringe image, the intensity modulator for applying intensity modulation to the first fringe image and producing a second fringe image in each of plural relative positions out of phase with one another with respect to a periodic pattern of the first fringe image, and an X-ray radiation image detector for detecting the second fringe image, the method comprising:
   capturing the second fringe image by the X-ray radiation image detector;
   obtaining an intensity modulation signal from a plurality of the captured second fringe images on a pixel-by-pixel basis;
   comparing a measurement of a characteristic value of the intensity modulation signal with a predetermined threshold value; and
   evaluating the positional deviation based on a comparison result.

* * * * *